US011351006B2

(12) United States Patent
Aferzon et al.

(10) Patent No.: US 11,351,006 B2
(45) Date of Patent: Jun. 7, 2022

(54) SYSTEM FOR STEREOSCOPIC VISUALIZATION ENABLING DEPTH PERCEPTION OF A SURGICAL FIELD

(71) Applicant: Orthozon Technologies, LLC, Stamford, CT (US)

(72) Inventors: Joshua Aferzon, Stamford, CT (US); Joseph Aferzon, Avon, CT (US); Lee M. Nicholson, Katonah, NY (US)

(73) Assignee: Orthozon Technologies, LLC, Stamford, CT (US)

( * ) Notice: Subject to any disclaimer, the term of this patent is extended or adjusted under 35 U.S.C. 154(b) by 0 days.

(21) Appl. No.: 15/607,035

(22) Filed: May 26, 2017

(65) Prior Publication Data
US 2017/0340405 A1  Nov. 30, 2017

Related U.S. Application Data

(60) Provisional application No. 62/342,108, filed on May 26, 2016.

(51) Int. Cl.
*A61B 90/00* (2016.01)
*H04N 13/239* (2018.01)
(Continued)

(52) U.S. Cl.
CPC ........... *A61B 90/37* (2016.02); *A61B 90/361* (2016.02); *A61B 90/50* (2016.02);
(Continued)

(58) Field of Classification Search
CPC ........ A61B 2090/371; A61B 2090/502; H04N 13/344; G02B 27/017; G02B 27/0172; G02B 27/0176; G02B 27/0178
See application file for complete search history.

(56) References Cited

U.S. PATENT DOCUMENTS

| 4,651,201 A | 3/1987 | Schoolman |
| 5,381,784 A | 1/1995 | Adair |

(Continued)

OTHER PUBLICATIONS

International Search Report and Written Opinion issued in International Application No. PCT/US2017/034791 dated Aug. 24, 2017.
(Continued)

*Primary Examiner* — Jayanti K Patel
*Assistant Examiner* — Christopher Kingsbury Glover
(74) *Attorney, Agent, or Firm* — Hoffmann & Baron, LLP

(57) ABSTRACT

Stereoscopic system including a portal component, first sensor and first cable, second sensor and second cable, first display and second display. The portal component includes an axis, a first channel and second channel extending along the axis. The first sensor is secured within the first channel at a first angle with respect to the axis and directed inwardly toward a location. The first cable extends from the first sensor. The second sensor is secured within the second channel at a second angle with respect to the axis and directed inwardly toward the location. The first angle and second angle converge at the location to define a depth of perception. The second cable extends from the second sensor. The first display structure is disposed in proximity to a left aperture of an eyeframe, and the second display structure is disposed in proximity to a right aperture of the eyeframe.

12 Claims, 11 Drawing Sheets

(51) Int. Cl.
*A61B 90/50* (2016.01)
*H04N 13/344* (2018.01)
*H04N 13/128* (2018.01)
*H04N 5/232* (2006.01)
*A61B 17/34* (2006.01)

(52) U.S. Cl.
CPC ....... *H04N 5/23296* (2013.01); *H04N 13/128* (2018.05); *H04N 13/239* (2018.05); *H04N 13/344* (2018.05); *A61B 17/3439* (2013.01); *A61B 2090/365* (2016.02); *A61B 2090/3616* (2016.02); *A61B 2090/3618* (2016.02); *A61B 2090/371* (2016.02); *A61B 2090/372* (2016.02); *A61B 2090/502* (2016.02); *H04N 2201/0079* (2013.01); *H04N 2213/001* (2013.01)

(56) References Cited

U.S. PATENT DOCUMENTS

| | | | |
|---|---|---|---|
| 5,712,649 A | 1/1998 | Tosaki | |
| 5,886,822 A | 3/1999 | Spitzer | |
| 5,926,318 A | 7/1999 | Herbert | |
| 6,356,392 B1* | 3/2002 | Spitzer | G02B 27/017 345/8 |
| 8,882,662 B2* | 11/2014 | Charles | A61B 1/00193 600/214 |
| 2004/0196553 A1 | 10/2004 | Banju et al. | |
| 2012/0014590 A1* | 1/2012 | Martinez-Bauza | G06T 7/97 382/154 |
| 2012/0280893 A1 | 11/2012 | Holakovszky | |
| 2013/0222384 A1* | 8/2013 | Futterer | G02B 5/32 345/426 |
| 2015/0123880 A1* | 5/2015 | Tam | G02B 25/004 345/8 |
| 2018/0176547 A1* | 6/2018 | Kobayashi | H04N 13/332 |
| 2020/0073110 A1* | 3/2020 | Maeda | G02B 25/02 |

OTHER PUBLICATIONS

European Search Report issued in European Application No. 17803706 dated Dec. 4, 2019.
English-language summary of Office Action issued in Chinese Patent Application No. 201780032274.0 dated Jul. 28, 2021.

* cited by examiner

SYSTEM FOR STEREOSCOPIC VISUALIZATION ENABLING DEPTH PERCEPTION OF A SURGICAL FIELD

CROSS REFERENCE TO RELATED APPLICATIONS

This application claims benefit of U.S. Provisional Patent Application No. 62/342,108, filed on May 26, 2016, the contents of which are incorporated herein by reference in their entirety.

BACKGROUND

Field

The present disclosure relates to surgical visualization systems. More specifically, the present application is directed to a system for stereoscopic visualization enabling depth perception of a surgical field, such as during surgery.

Brief Discussion of Related Art

Minimally invasive surgical techniques utilize portals (e.g., retraction devices or simply retractors) to perform medical procedures through small incisions in a patient. When compared to open surgical techniques with large incisions, minimally invasive surgical techniques reduce tissue trauma, blood loss, surgical duration, probability of infection, as well as post-operative medication usage, leading to significant benefits for patients, surgeons, and hospitals.

As surgeons become more proficient with these techniques, the opening of the portals (e.g., diameter of retractors) can be reduced further to more accurately and acutely target the anatomy of the patient. However, the reduction of the opening into the patient greatly reduces a surgeon's visibility through the portal into the surgical field. Surgical loupes are a commonly used magnification technology, which includes binocular lenses that are attached to an eyeframe. However, surgical loupes are becoming increasingly less useful because of the limited visibility through such reduced-opening portals in minimally invasive surgical techniques. As such, new minimally invasive techniques generally rely on digital image data from cameras—of various camera technologies—disposed in the surgical field. The digital image data of a camera is generally presented on a standalone display screen, which is typically attached to the bed side of the patient. The cameras are typically monoscopic and accordingly do not enable depth perception, which is critical in discriminating the various anatomic structures inside the patient.

There exist surgical microscopes that allow stereoscopic vision. However, such microscopes are extremely bulky, non-mobile, and are frequently cost-prohibitive to small hospitals, surgical centers, and private physicians, which perform the majority of the minimally invasive procedures. Moreover, microscopes are not natural to a surgeon and require deviation of the surgeon's position and attention from the surgical field as viewed on the display screen to a surgical field as viewed through a separate microscope, and back again, in order to discriminate the various anatomic structures inside the patient. The foregoing is not efficient and presents certain dangers because such switching requires the surgeon to remember and combine the disparate views as the surgeon switches his/her position and attention.

Moreover, the foregoing visualization technologies are not designed to interact with specific minimally invasive portals, making alignment of the cameras and microscopes to target structures time-consuming and complex. Due to the lack of available options, many surgeons simply resort to performing procedures with larger incisions in order to provide the best possible visualization of the surgical field. However, the larger incisions can negatively affect the patients' recovery and generate larger than necessary scarring from the incisions.

Human binocular vision allows for depth perception. This requires presentation of the same image to both eyes of the human under slightly different angles. The slight difference in image projection, or parallax, to each eye can provide the surgeon's brain with relative depth information of the anatomical structures in the surgical field. More specifically, during surgery, surgeons are required to interact with small, sensitive tissues and structures, such as blood vessels, nerves, ligaments, and muscles that, if injured, could result in severe patient injury or death. Current monoscopic visualization technologies do not offer surgeons depth perception, and affect negatively the ability of the surgeons to distinguish between the anatomical structures in the surgical field, especially where the structures are intertwined, hard-to-access, and/or poorly lit.

It is therefore desirable to provide an interactive, easy to use system for stereoscopic visualization that enables depth perception of a surgical field using a surgeon's natural binocular vision without requiring separate microscopes.

SUMMARY

The stereoscopic visualization portal system presented in this disclosure delivers respective image data to the surgeon enabling stereoscopic image formation in a natural binocular fashion that easily integrates into routine surgical procedures such as minimally invasive surgical procedures, without the associated difficulty and costs associated with using current technologies in connection with minimally invasive portals, including technologies such as surgical loupes, standalone displays, as well as stereoscopic microscopes.

The stereoscopic visualization portal system includes a portal component, a first image sensor and a first cable, a second image sensor and a second cable, a first display structure and a second display structure.

The portal component includes an axis and a plurality of channels, wherein the channels include a first channel and a second channel extending along the axis.

The first image sensor is secured within the first channel at a first angle with respect to the axis and is directed inwardly toward a location. The first cable extends from the first image sensor to transmit first image data.

The second image sensor is secured within the second channel at a second angle with respect to the axis and is directed inwardly toward the location. The first angle and the second angle converge at the location to define a depth of perception. The second cable extends from the second image sensor to transmit second image data.

The first display structure is disposed in proximity to a left aperture of an eyeframe to present the first image data through the left aperture, and the second display structure is disposed in proximity to a right aperture of an eyeframe to display the second image data through the right aperture.

A view that is external to the first display structure and the second display structure is visible through the first aperture and the second aperture. Moreover, the first image data and the second image data are visible through the first aperture and the second aperture enabling formation of a stereoscopic view of a structure disposed within the depth of perception.

In some cases, the first display structure and the second display structure can be angulated with respect to the eyeframe. Moreover, the first display structure and the second display structure can be angulated with respect to each other.

The system can further include a frame, a first display aperture, and a second display aperture. The frame can include a first eye aperture and a second eye aperture. Moreover, the first display aperture can be proximate to the first eye aperture, and the second display aperture can be proximate to the second eye aperture.

The system can also include a first magnifying apparatus, a first electronic display, a second magnifying apparatus, and a second electronic display. The first magnifying apparatus can be disposed in relation to the first display aperture and can be connected to the first electronic display at a first end of the first magnifying apparatus, while the second magnifying apparatus can be disposed in relation to the second display aperture and can be connected to the second electronic display at a first end of the first magnifying apparatus.

Moreover, the first display structure can include a first mirror structure disposed proximately to a second end of the first magnifying apparatus, and the second display structure can include a second mirror structure disposed proximately to a second end of the second magnifying apparatus.

The first mirror structure can include a first mirror and a second mirror. The first mirror and the second mirror can each be angled at forty five degrees with respect to a vertical plane separating the first mirror from the second mirror, and the second mirror can be disposed proximately to the first eye aperture.

The second mirror structure can include a first mirror and a second mirror. The first mirror and the second mirror can each be angled at forty five degrees with respect to a vertical plane separating the first mirror from the second mirror, and the second mirror can be disposed proximately to the second eye aperture.

The first display structure can include a first magnifying apparatus and a first electronic display. The first magnifying apparatus can be disposed in relation to the first display aperture at a first end of the first magnifying apparatus and proximately to the first electronic display at a second end of the first magnifying apparatus. The second display structure can include a second magnifying apparatus and a second electronic display. The second magnifying apparatus can be disposed in relation to the second display aperture at a first end of the second magnifying apparatus and proximately to the second electronic display at a second end of the second magnifying apparatus.

The system can further include a processing device that includes a first incoming data port configured to receive the first image data and a second incoming data port configured to receive the second image data. The first incoming data port can be connected to the first cable and the second incoming data port can be connected to the second cable. The processing device can further include a first outgoing data port configured to transmit the first image data to the first electronic display and a second outgoing data port configured to transmit the second image data to the second electronic display.

These and other purposes, goals, and advantages of the present disclosure will become apparent from the following detailed description read in connection with the accompanying drawings.

BRIEF DESCRIPTION OF DRAWINGS

The accompanying drawings are presented to aid in the description of embodiments of the disclosure and are provided solely for illustration of the embodiments and not limitation thereof.

DETAILED DESCRIPTION

Described herein are a system and method for stereoscopic visualization that enables depth perception of a surgical field. The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

Figure 1A:
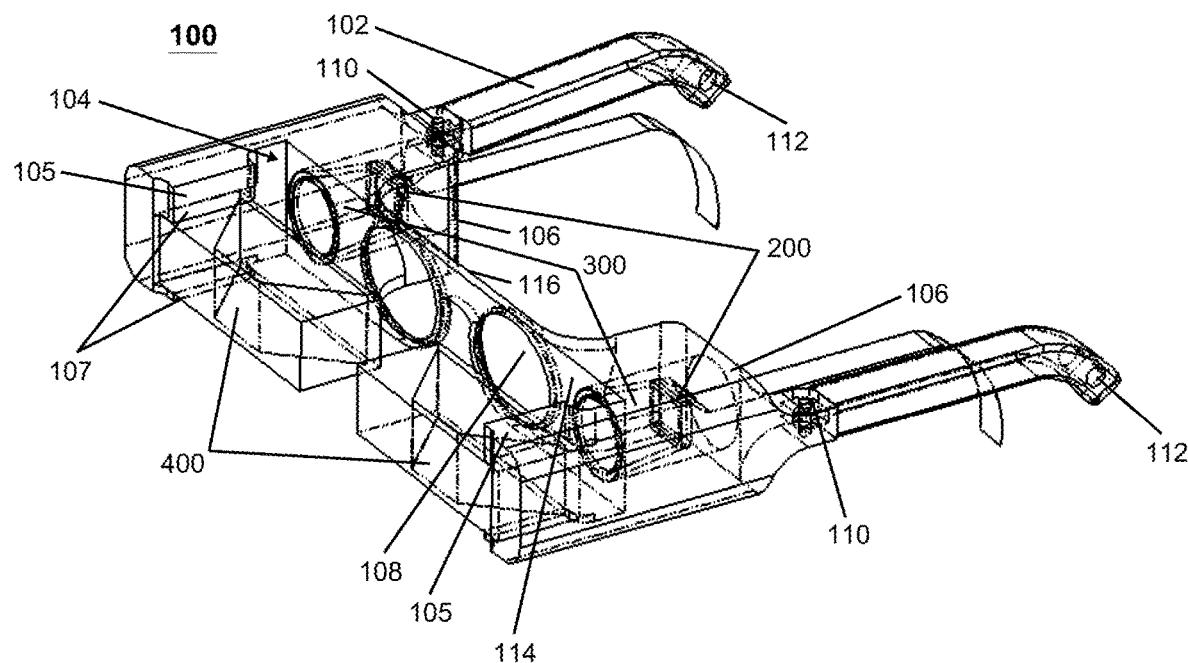
FIG. 1A illustrates a front perspective view of an example stereoscopic apparatus of a stereoscopic visualization portal system.

FIG. 1A illustrates a front perspective view of an example stereoscopic apparatus 100 of a stereoscopic visualization portal system. The apparatus 100 includes a frame 104, electronic displays 200, magnifying apparatuses 300, and mirror structures 400.

As illustrated in FIG. 1A, the frame 104 includes electronic display housings 106, an eyeframe 108, and holders 105. The frame 104 also defines a back wall 116 and a front wall 114, which extend from the eyeframe 108 to the electronic display housings 106. The frame 104 may be made from a material such as a polymer, metal, ceramic, or composites of one or more thereof. One or more other materials may be used for the frame 104.

The electronic display housings 106 are disposed on the sides of the eyeframe 108. Each electronic display housing 106 includes an aperture that extends from the back wall 116 to the front wall 114 of the frame 104 (e.g., back wall to front wall of the housing 106), and is configured to house a respective electronic display 200 and a respective magnifying apparatus 300.

A respective earpiece attachment 110 extends from or attaches to the back wall 116 of the frame 104 (e.g., back wall of the housing 106), allowing counter-balancing of the stereoscopic apparatus 100 comfortably on the surgeon's face and ears. Moreover, a respective earpiece 102 extends from each earpiece attachment 110 beyond the surgeon's ear, with a hook section 112, configured to secure the frame 104 over the surgeon's face and ears. In some cases, the earpiece attachments 110 can be omitted, where the earpieces 102 extend from or attach to the back wall 116 of the frame 104 (e.g., back wall of the respective housings 106).

The eyeframe 108 includes two apertures (e.g., circular, elliptical, rectangular, another shape, or any combination of shapes) extending from the back wall 116 to the front wall 114 of the frame 104 (e.g., back wall to front wall of the eyeframe 108). The apertures are configured to allow the surgeon to see individual displays through the apertures of the eyeframe 108, which in combination allow the surgeon to form a stereoscopic view that enables depth perception of a surgical field. The apertures of the eyeframe 108 can hold non-prescription lenses, or prescription lenses based on the surgeon's eyesight.

The holders 105 extend from or attach to the front wall 114 of the frame 104 (e.g., front wall of the housing 106). Mirror structures 400 are attached to the frame 104 in front of and partially below the eyeframe 108 via the holders 105, allowing the surgeon to see the surrounding external view about the apparatus 100 through the apertures of the eyeframe 108 and over mirror structures 400. More specifically, a holder 105 can include one or more arms 107 to which or between which a mirror structure 400 can be secured. For example, the holder 105 includes one arm that extends at the top and one arm that extends at the bottom of the holder, and the mirror structure 400 is secured between the arms 107. The mirror structure 400 can be secured with respect to the arms 107 using one or more of glue, screws, bolts, or friction fit.

The mirror structures 400, which can also be described as display structures, provide respective image data from the electronic displays 200 as captured by respective cameras disposed in the surgical field, or respective magnified image data resulting from a combination of the electronic displays 200 and respective magnifying apparatuses 300, allowing the surgeon to see the respective image data of the surgical field through the apertures of the eyeframe 108 and via mirror structures 400. It should be noted that while the left and right mirror structures 400 are shown as two separate mirror structures, these mirror structures can also be one monolithic structure extending between mirror holders 105 that includes the two mirror structures 400.

The mirror structures 400 are angulated at an angle defined from a front plane of the mirror structure 400 (FIG. 6) to a plane of the front wall 114 of the frame 104, or an angle to a plane of a lens secured in the aperture of the eyeframe 108. As illustrated in FIG. 1A, the angle can be zero (0) degrees. Larger angulations will be described in greater detail with reference to FIG. 3C.

Figure 1B:
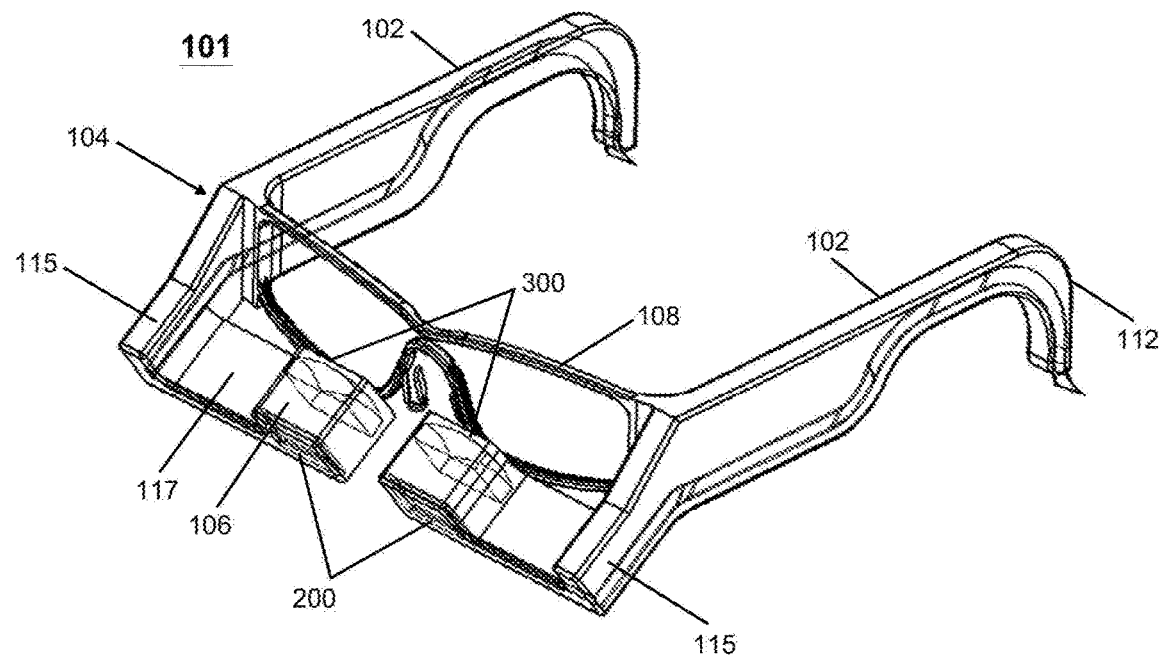
FIG. 1B illustrates a front perspective view of another example stereoscopic apparatus of a stereoscopic visualization portal system.

FIG. 1B illustrates a front perspective view of another example stereoscopic apparatus 101 of a stereoscopic visualization portal system. The apparatus 101 includes a frame 104, electronic displays 200, and magnifying apparatuses 300.

The frame 104 includes an eyeframe 108 and holders 115. The frame 104 may be made from a material such as a polymer, metal, ceramic, or composites of one or more thereof. One or more other materials may be used for the frame 104.

The holders 115 extend from or attach to the front of the eyeframe 108. The electronic display housings 106, which can also be described herein as display structures, are attached in front of and partially below the eyeframe 108 via the holders 115, allowing the surgeon to see the surrounding external view through the apertures of the eyeframe 108 and over electronic display housings 106. More specifically, a holder 115 can include an arm 117 to which the electronic display housing 106 is secured. For example, the holders 105 include arms 117 that extend at the bottom of the holders 105, and the electronic display housings 106 are disposed along terminal portions of the arms 117 and toward a center of the eyeframe 108, allowing the surgeon to see the surroundings external to the apparatus 100 with greater visibility through the apertures of the eyeframe 108, over arms 117 and the electronic display housings 106.

In some cases, the holders 115 can slope down from the eyeframe 108, which allows the arms 117 and the electronic display housings 106 to be angulated with respect to the eyeframe 108, providing improved visibility of the surroundings external to the apparatus 100 when the surgeon looks straight through the eyeframe 108, and also excellent visibility of the surgical field when the surgeon looks down through the eyeframe 108 into the electronic display housings 106.

It should be noted that the holders 115 do not have to slope down from the eyeframe 108 in order for the arms 117 and/or the electronic display housings 106 to be angulated with respect to the eyeframe 108. In some cases, the holders 115 can extend straight from the eyeframe 108, but the arms 117 can be rotated with respect to the holders 115 in accordance with the desired angulation to the electronic display housings 106. In some other cases, the holders 115 can extend straight from the eyeframe 108 and arms 117 can also extend without rotation from the holders 115, but the electronic display housings 106 can be rotated with respect to the arms 117 in accordance with the desired angulation to the eyeframe.

The electronic display housing 106 can be angulated at an angle defined from a front plane of the display housing 106 (FIG. 3B) to a front plane of the eyeframe 108, or an angle to a front plane of a lens secured in the aperture of the eyeframe 108. The angle may be in the range of about zero (0) degrees to about thirty (30) degrees. A preferred range can also be in a range of about seventeen (17) degrees to about twenty-two (22) degrees. Since the electronic display housings 106 are angled away from the frame 104, this provides improved visibility of the surroundings external to the apparatus 101 when a surgeon looks straight through the eyeframe 108, and visibility of the surgical field when the surgeon looks down through the eyeframe 108 into electronic display housing 106.

Each electronic display housing 106 includes an aperture that extends from the back of the housing 106 toward the eyeframe 108, and is configured to house a respective electronic display 200 and a respective magnifying apparatus 300. The electronic displays 200 can provide respective image data to the surgeon's eyes as captured by respective cameras disposed in the surgical field, or respective magnified image data resulting from a combination of the electronic displays 200 and respective magnifying apparatuses 300 can be provided to the surgeon's eyes. While the left and right arm/housing combinations are shown as two separate structures, these structures can also be one monolithic structure that includes an arm extending between the holders 115 and attaching the housings 106.

The earpieces 102 extend beyond the surgeon's ears, with a hook sections 112 configured to secure the frame 104 over the surgeon's face and ears.

The eyeframe 108 includes two apertures (e.g., circular, elliptical, rectangular, another shape, or any combination of shapes). The apertures are configured to allow the surgeon to see individual displays through the apertures of the eyeframe 108, which in combination allow the surgeon to form a stereoscopic view that enables depth perception of a surgical field. The apertures of eyeframe 108 can hold non-prescription lenses, or prescription lenses based on the surgeon's eyesight.

Figure 2A:
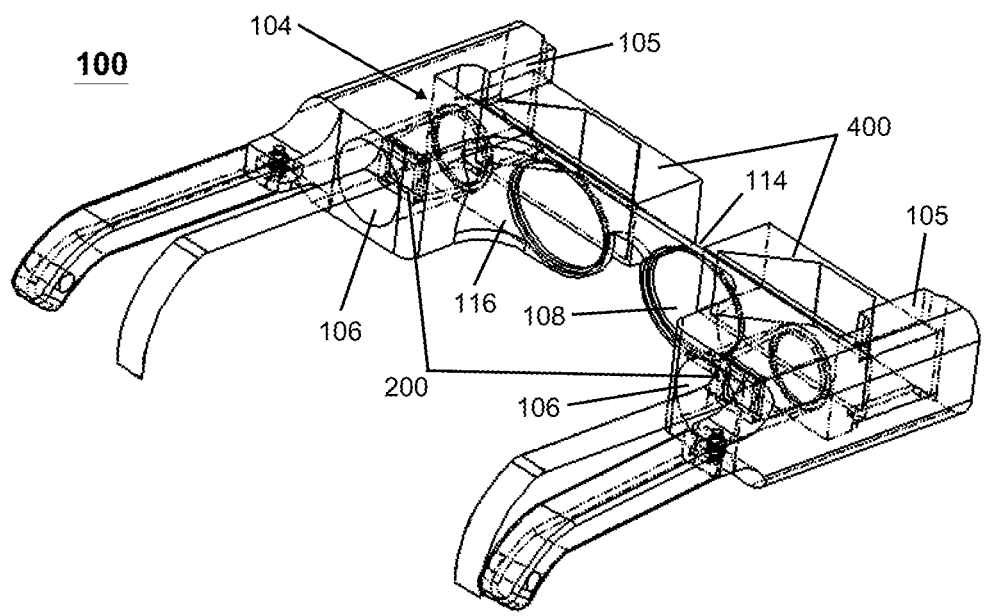
FIG. 2A illustrates a rear perspective view of the example stereoscopic apparatus of FIG. 1A.
Figure 3A:
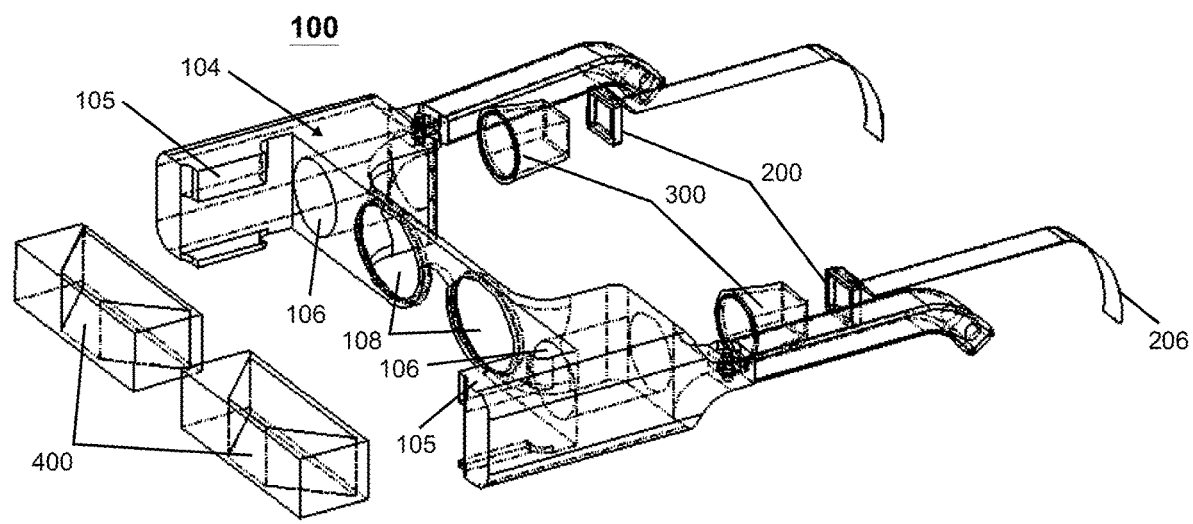
FIG. 3A illustrates an exploded view of the example stereoscopic apparatus of FIG. 1A.

FIG. 2A illustrates a rear perspective view of the example stereoscopic visualization apparatus 100 of a stereoscopic visualization portal system, while FIG. 3A illustrates an exploded view of the stereoscopic visualization apparatus 100 that shows the individual electronic displays 200, magnifying apparatuses 300, and mirror structures 400 in greater detail.

As particularly illustrated in FIGS. 1A, 2A, and 3A, a surgeon can see the surrounding external view through the apertures of the eyeframe 108 and over the mirror structures 400. This is important so that the surgeon can use the eyeframe 108 to view the surroundings external to the apparatus 100 (e.g., surgical theater or operating room), while also being able to easily switch the surgeon's view instantaneously to the surgical field without shifting his/her position and allowing the surgeon to maintain attention to the particular structures in the surgical field when switching among the views.

Figure 2B:
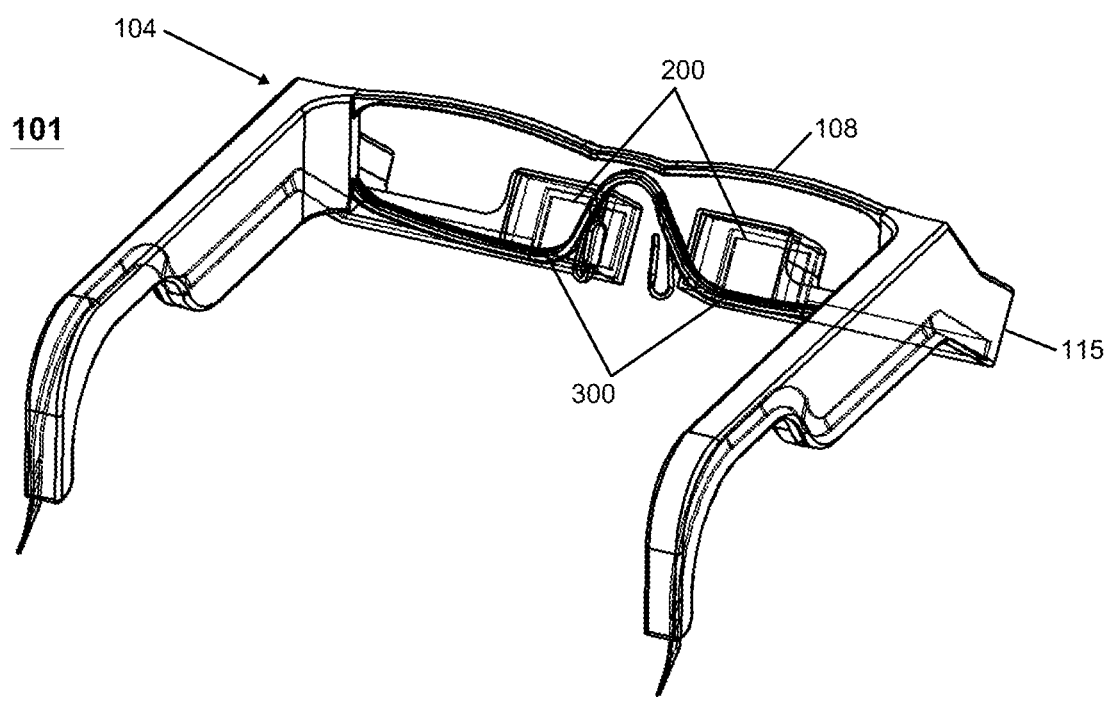
FIG. 2B illustrates a rear perspective view of the other example stereoscopic apparatus of FIG. 1B.
Figure 3B:
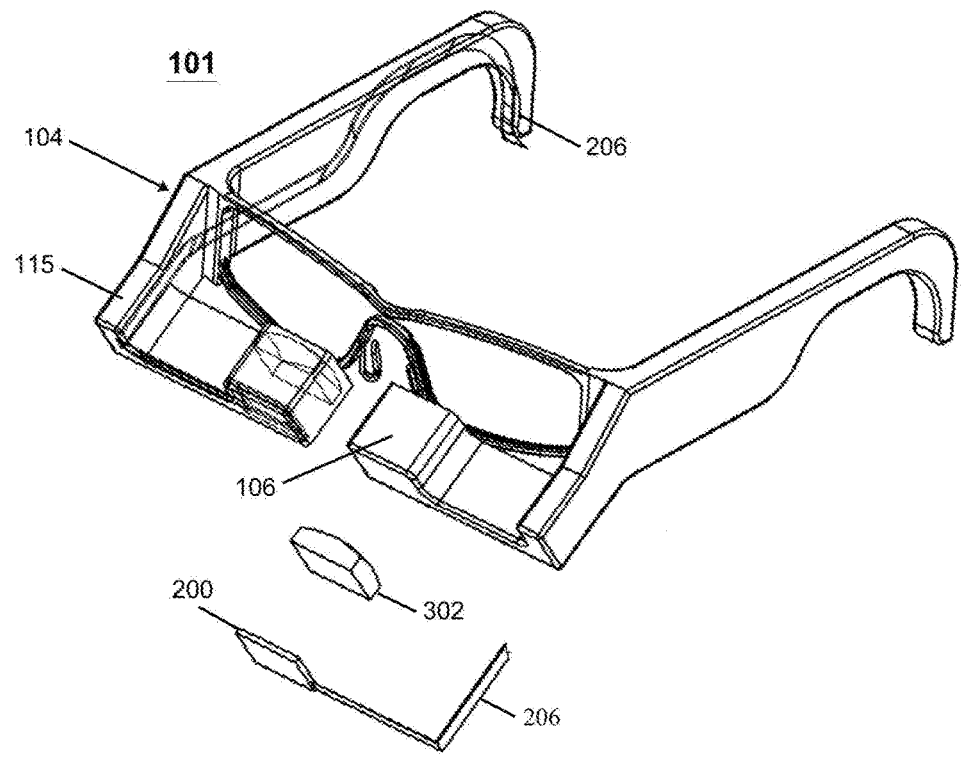
FIG. 3B illustrates an exploded view of the other stereoscopic apparatus of FIG. 1B.

FIG. 2B illustrates a rear perspective view of the example stereoscopic visualization apparatus 101 of a stereoscopic visualization portal system, while FIG. 3B illustrates an exploded view of the stereoscopic visualization apparatus 101 that shows the individual electronic displays 200 and magnifying apparatuses 300.

The example magnifying apparatus 300 of the stereoscopic visualization apparatus 101 includes one or more magnifying lenses 302 (e.g., generally referred to as a magnifying lens 302). Light is allowed to extend through the aperture of the housing 106 and passes onto the magnifying lens 302. The magnifying lens 302 is disposed adjacently to the screen 202 (FIG. 4B) of the electronic display 200 to receive the image output of the electronic display 200.

As the light travels through the magnifying lens 302, image data is magnified or de-magnified into a resulting image for view by the surgeon. The resulting image (magnified or de-magnified) exits the housing 106 and travels to the surgeon's eyes through the apertures of the eyeframe 108 (e.g., with or without lenses).

More specifically, the magnifying lens 302 bends incoming light from the electronic screen and forms a magnified image output for the surgeon's eyes. This resulting image will appear farther away to the surgeon than the screen 202 without the presence of a magnifying lens 302, thereby enabling the surgeon to resolve the image properly, similarly to a regular pair of prescription eyeglass lenses. The magnifying lens 302 may be composed of an acrylic, glass, crystal, a composite thereof, or other polymers with glass properties. The magnifying lens 302 may further comprise an anti-reflective coating to prevent external light waves from interfering with the transmission of the image from the screen 202 through the magnifying lens 302.

As particularly illustrated in FIGS. 1B, 2B, and 3B, a surgeon can see the surrounding external view through the apertures of the eyeframe 108 and over the electronic display housing 106. As already described hereinabove, this is important so that the surgeon can use the eyeframe 108 to view surroundings external to the apparatus 101 (e.g., surgical theater or operating room), while also being able to easily switch the surgeon's view instantaneously to the surgical field without shifting his/her position and allowing the surgeon to maintain attention to the particular structures in the surgical field when switching among the views.

Figure 3C:
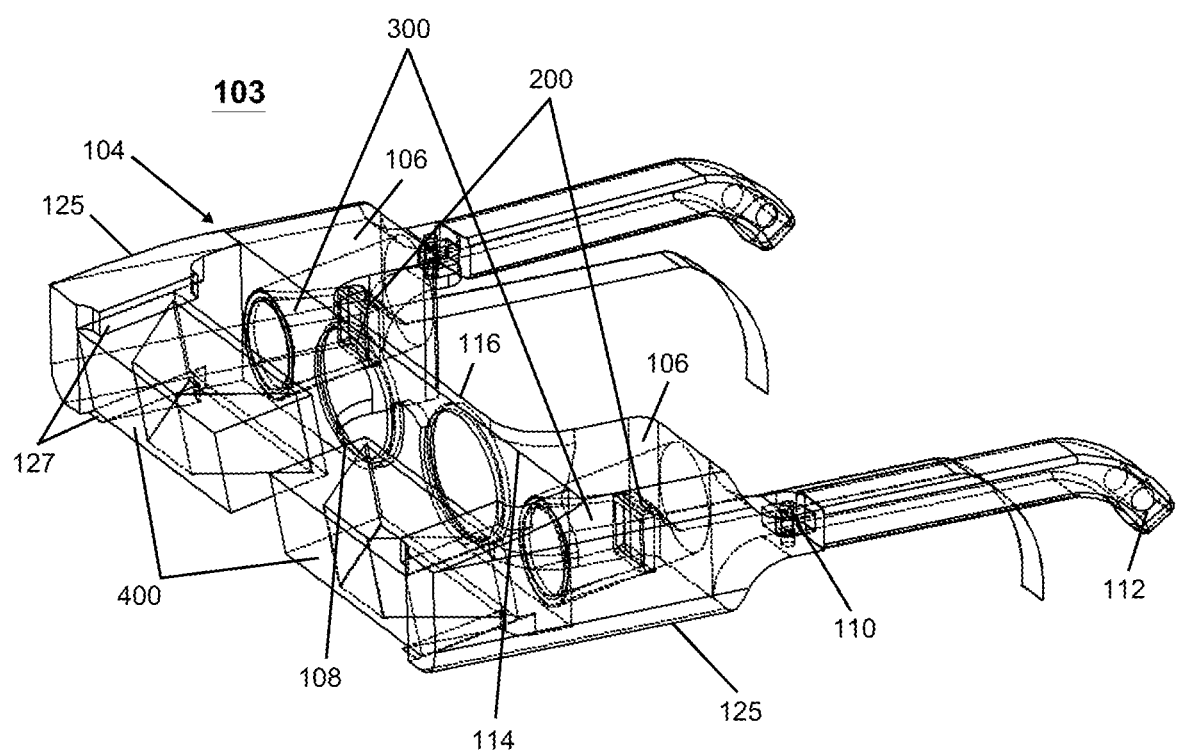
FIG. 3C illustrates a front perspective view of yet another example stereoscopic apparatus of a stereoscopic visualization portal system.

FIG. 3C illustrates a front perspective view of yet another example stereoscopic apparatus 103 of a stereoscopic visualization portal system. The apparatus 100 includes a frame 104, electronic displays 200, magnifying apparatuses 300, and mirror structures 400.

The apparatus 103 is constructed similarly to the apparatus 100 of FIGS. 1A, 1B, and 1C, except that the holders 125 can slope down from the frame 104, which allows the arms 127 and the mirror structures 400 to be angulated with respect to the frame 104, providing improved visibility of the surroundings external to the apparatus 103 (e.g., surgical theater or operating room) when a surgeon looks straight through the eyeframe 108, and also the visibility of the surgical field when the surgeon looks down through the eyeframe 108 into mirror structures 400.

The combination of the electronic displays 200 and magnifying apparatuses 300 can also be angulated in the electronic display housings 106 so that resulting image data from this combination can travel at a zero-degree orientation into the mirror structure 400.

It should be noted that the holders 125 do not have to slope down from the frame 104 in order for the arms 127 to be angulated with respect to the frame 104. In some cases, the holders 125 can extend straight from the frame 104, but the arms 127 can be rotated with respect to the holders 125 in accordance with the desired angulation of the mirror structures 400.

The mirror structures 400 can be angulated at an angle defined from a front plane of the mirror structure 400 (FIG. 6) to a plane of the front wall 114 of the frame 104, or an angle to a plane of a lens secured in the aperture of the eyeframe 108. The angle may be in the range of about zero (0) degrees to about thirty (30) degrees. A preferred range can also be in a range of about seventeen (17) degrees to about twenty-two (22) degrees. Since mirror structures 400 are angled away from the frame 104, this provides improved visibility of the surrounding external view about the apparatus 103 when a surgeon looks straight through the eyeframe 108, and visibility of the surgical field when the surgeon looks down through the eyeframe 108 into mirror structure 400.

Figure 4A:
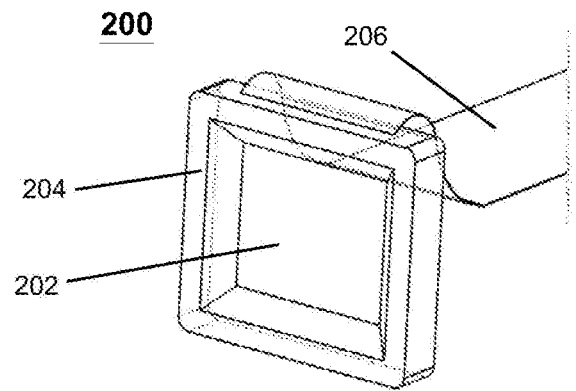
FIG. 4A illustrates an example electronic visual display of the stereoscopic apparatus of FIG. 1A.
Figure 12A:
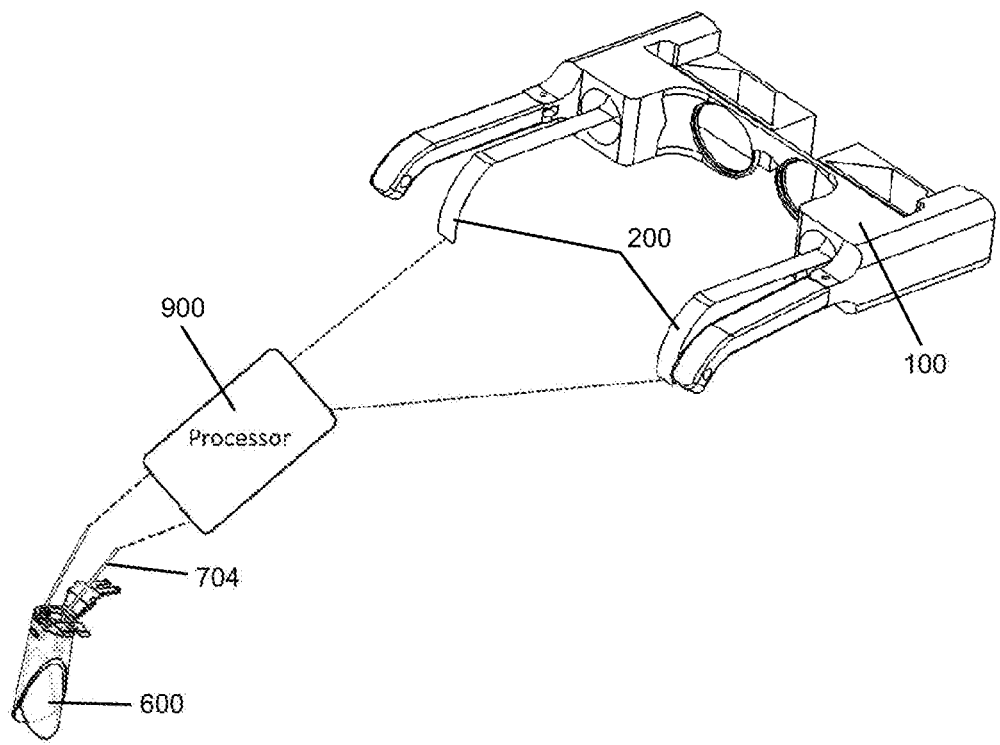
FIG. 12A illustrates an example stereoscopic portal system connected to an electronic processor and the example stereoscopic apparatus of FIG. 1A.

FIG. 4A illustrates an example electronic display 200 of the example stereoscopic apparatus 100. The electronic display 200 includes a screen 202, a screen housing 204, and a data cable 206. The screen 202 may be include a liquid crystal display (LCD), a light emitting diode (LED), a cathode ray tube (CRT), or an alternative display capable of projecting light composed in a pattern, for example, as determined by a processor (e.g., processing device) 900 (FIG. 12A).

As illustrated in FIG. 4A, the screen housing 204 encloses the screen 202 to protect the screen 202 from wear and repeated use. The data cable 206 is attached to the screen 202 and transmits image data from the processor (e.g., processing device) 900 to the screen 202. In some cases, the data cable 206 can be attached at the top as illustrated in FIG. 4A, or can be attached at the bottom, left, or right, as might be desired by the form factor of the example stereoscopic apparatus 100. The respective screens 202 project the transmitted respective (left and right) image data to the surgeon to enable stereoscopic visualization that enables depth perception of a surgical field using a surgeon's natural binocular vision.

Figure 4B:
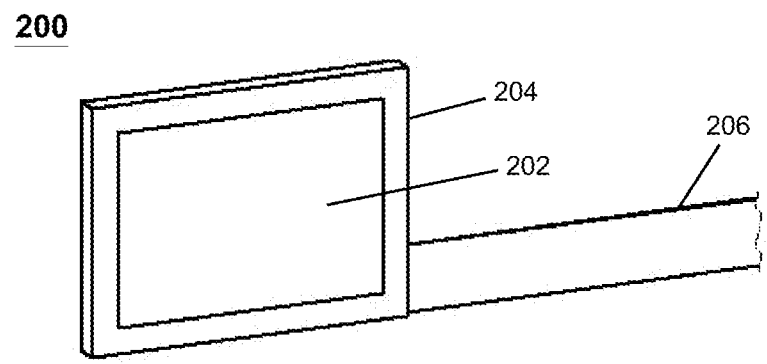
FIG. 4B illustrates another example electronic visual display of the stereoscopic apparatus of FIG. 1B.
Figure 12B:
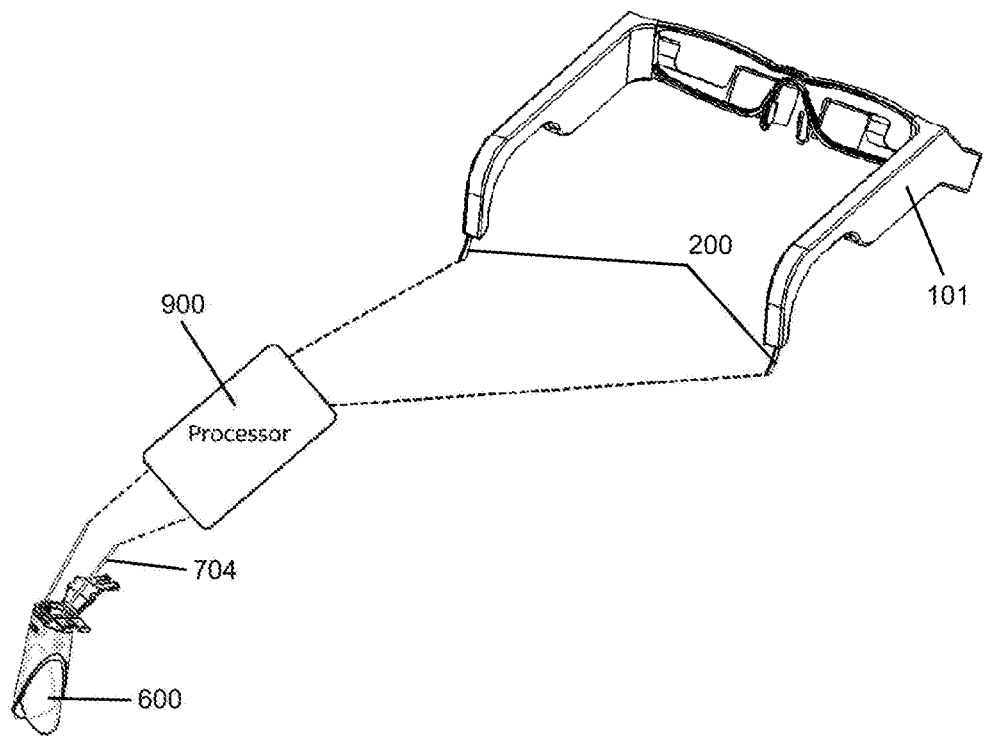
FIG. 12B illustrates an example stereoscopic portal system connected to an electronic processor and the example stereoscopic apparatus of FIG. 1B.

FIG. 4B illustrates the example electronic display 200 of the example stereoscopic apparatus 101. Similarly, the electronic display 200 includes a screen 202, a screen housing 204, and a data cable 206. The screen 202 may be include a liquid crystal display (LCD), a light emitting diode (LED), a cathode ray tube (CRT), or an alternative display capable of projecting light composed in a pattern, for example, as determined by a processor (e.g., processing device) 900 (FIG. 12B).

Figure 5:
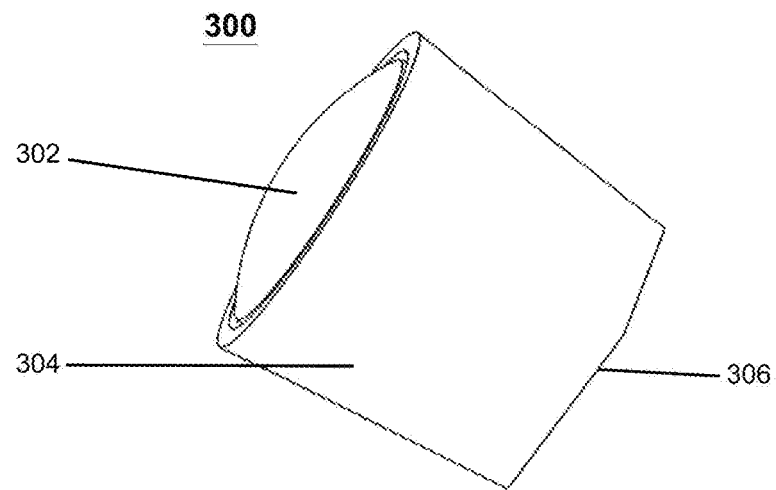
FIG. 5 illustrates example magnifying apparatuses of the stereoscopic apparatus of FIG. 1A.

As illustrated in FIG. 4B, the screen housing 204 encloses the screen 202 to protect the screen 202 from wear and repeated use. The data cable 206 is attached to the screen 202 and transmits image data from the processor (e.g., processing device) 900 to the screen 202. In some cases, the data cable 206 can be attached at the right as illustrated in FIG. 4B or at the left for the opposite electronic display 200, or can be attached at the bottom or top, as might be desired by the form factor of the example stereoscopic apparatus 101. The respective screens 202 project the transmitted respective (left and right) image data to the surgeon to enable stereoscopic visualization that enables depth perception of a surgical field using a surgeon's natural binocular vision FIG. 5 illustrates an example magnifying apparatus 300 of example stereoscopic apparatus 100 in greater detail. The magnifying apparatus 300 includes one or more magnifying lenses 302 (e.g., generally referred to as a magnifying lens 302), a housing 304, and an aperture 306.

The aperture 306 extends through the housing 304 and allows light to pass through the housing 304 and onto the magnifying lens 302. The aperture 306 is disposed adjacently (e.g., connected) to the screen 202 of the electronic display 200 to receive the image output of the electronic display 200.

As the light travels through the aperture 306 and the magnifying lens 302, image data is magnified or de-magnified into a resulting image for view by the surgeon. The resulting image (magnified or de-magnified) exits the magnifying apparatus 300 and travels to the mirror structure 400 for reflection to the surgeon through the apertures of the eyeframe 108 (e.g., with or without lenses).

Figure 6:
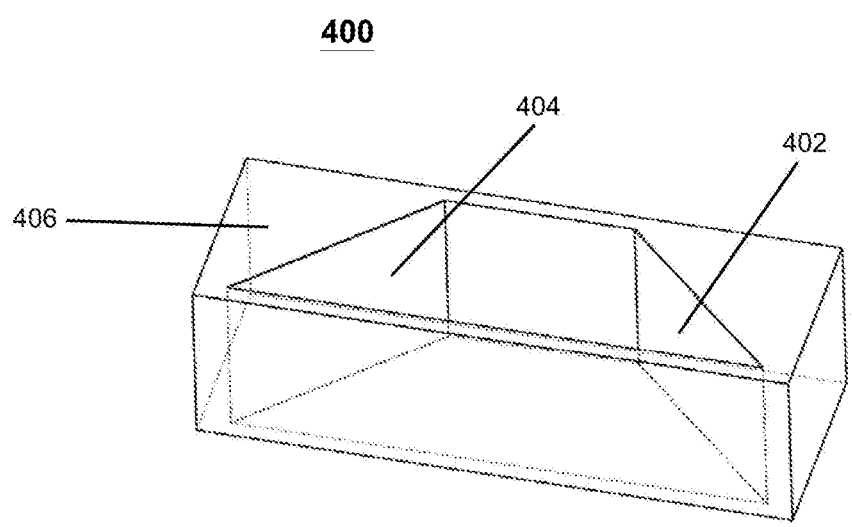
FIG. 6 illustrates example reflective mirrors of the stereoscopic apparatus 101 of FIG. 1A.

FIG. 6 illustrates an example mirror structure 400 of example stereoscopic apparatus 100. The mirror structure includes a first mirror 402, a second mirror 404, and a mirror housing 406.

The first mirror 402 and second mirror 404 are slanted towards one another at opposing forty-five degree angles with respect to a vertical plane separating the first mirror from the second mirror (total of 90 degrees), in order to transmit the resulting image (magnified or de-magnified) to the surgeon's eye. The mirror housing 406 maintains the angular position of the first mirror 402 and second mirror 404. The mirror housing 406 may be made from a material such as a polymer, metal, ceramic, or composites of one or more thereof.

The resulting image travels from the magnifying apparatus 300 along its original zero-degree orientation into the mirror structure 400. The image resulting is reflected off of the first mirror 402 and then travels at a ninety-degree angle to the second mirror 404.

The second mirror 404 then reflects the resulting image another ninety degrees to complete a one hundred and eighty degree reflection of the resulting image into the surgeon's eye.

Figure 7:
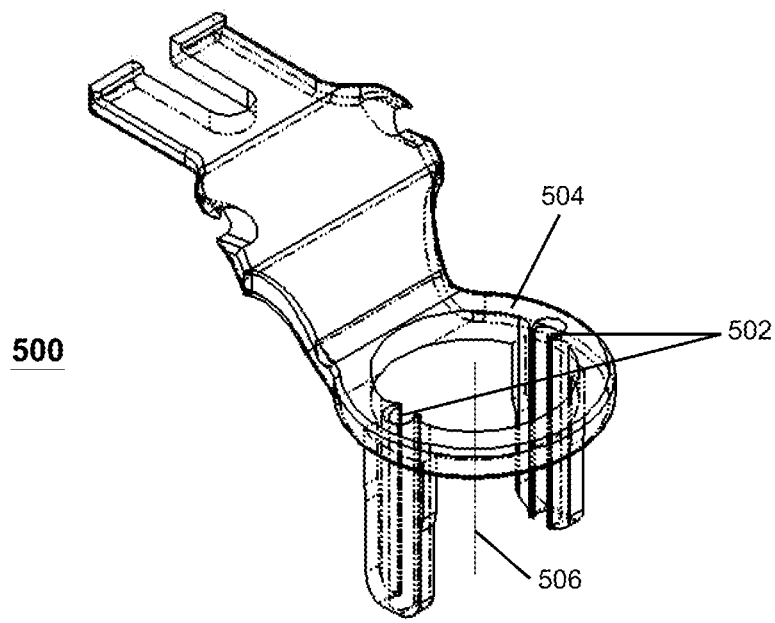
FIG. 7 illustrates an example portal component of a minimally invasive portal system.

FIG. 7 illustrates an example portal component 500 that includes a plurality of channels 502 and an aperture 504. The channels 502 receive and rigidly secure image sensors 700 (FIG. 10) that capture image data in the surgical field. The portal component 500 has an axis 506 about which the aperture 504 is defined and along which channels 502 extend.

The image sensors 700 can be secured in the channels 502 at a precise parallax angle ($\alpha$) so as to produce image data that can enable a surgeon to view a three dimensional image with depth perception in the surgical field using the surgeon's natural binocular vision. The channels 502 are disposed about the aperture 504, which can be connected to a minimally invasive portal. As illustrated in FIG. 7, the channels 502 are disposed at 180-degrees from one another about the aperture 504. However, other locations are of course possible.

In order to accomplish a more natural binocular vision experience (e.g., convergence of separate image data) for the surgeon, the electronic display housings 106 can be disposed inwardly with respect to each another using a relative angulation among these electronic display housings 106. More specifically, the relative angulation among the electronic display housings 106 can be defined to be proportional with respect to the parallax angle ($\alpha$) and distance between the cameras in the channels 502 of the portal component 500.

Figure 8:
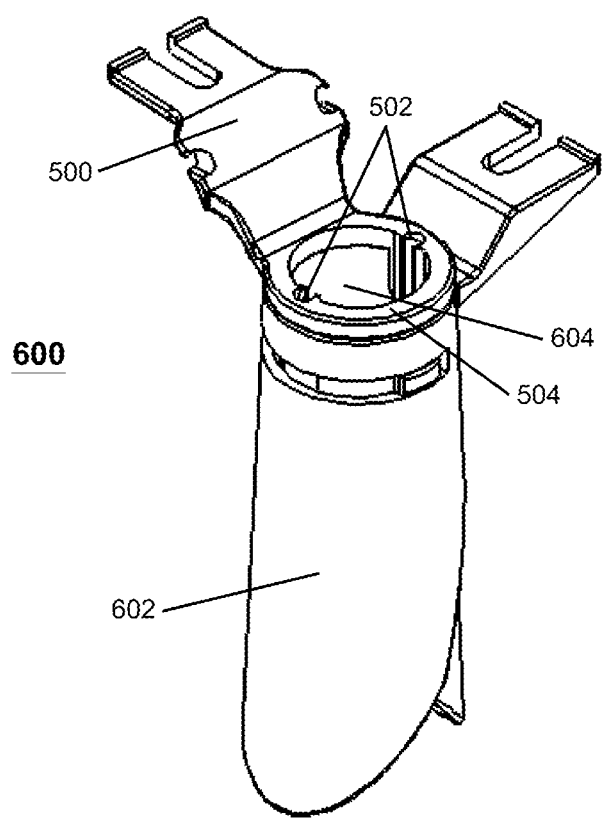
FIG. 8 illustrates a perspective view of a minimally invasive portal system that includes the portal component of FIG. 7.

FIG. 8 illustrates a minimally invasive portal system 600 that includes a minimally invasive portal 602 connected to the portal component 500.

The minimally invasive portal 602 may be cylindrical or conical, and includes an aperture 604 that is at least as large as the aperture 504 of the component 500. The purpose of the minimally invasive portal 602 is to split tissue apart and create a surgical channel in the body of the patient through which a surgeon can insert instrumentation and perform a procedure on a patient.

As illustrated in FIG. 8, the channels 502 of the portal component 500 extend through the minimally invasive portal 602 and are oriented directly towards anatomical structures of the patient that are of interest to the surgeon. It should be noted that the aperture 604 of the minimally invasive portal system 600 is generally too small for a surgeon to safely visualize anatomical structures of interest, which creates the need for advanced visualization as disclosed herein.

Figure 9:
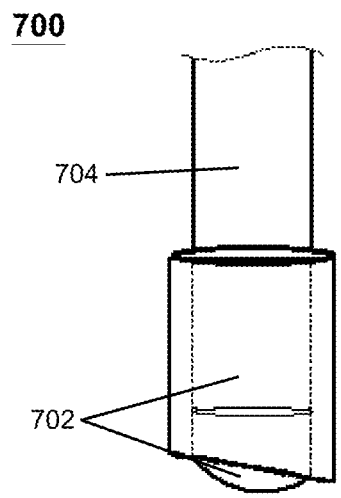
FIG. 9 illustrates an example image sensor.

FIG. 9 illustrates an example image sensor 700 including an image receiver 702 and an image data cable 704.

The image receiver 702 may be made of a complementary metal-oxide-semiconductor (CMOS), or an alternate circuit that captures image data.

The image data cable 704 transmits the image data (e.g., video), captured by the image receiver 702 to a processor (e.g., processing device) 900 (FIGS. 12A and 12B). It should be noted that respective image receivers 702 receive respective image data that are transmitted to the processor (e.g., processing device) 900.

Figure 10:
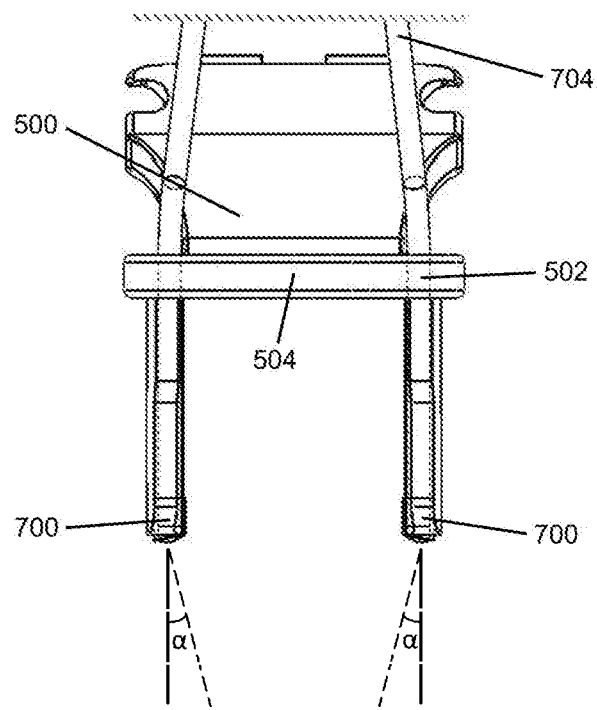
FIG. 10 illustrates a plurality of image sensors disposed in relation to the portal component of FIG. 7.

FIG. 10 illustrates a plurality of image sensors 700 disposed within the channels 502 of the portal component 500.

The channels 502 rigidly secure the image receivers 702 at inward angles marked (α), which can be identical. The angle α can range from about zero degrees to about 90 degrees for the purpose of creating two distinct images at a parallax.

The angle (α) can vary for different surgical procedures, but generally will be in a range of about zero degrees to about 10 degrees. More specifically, the angle (α) generally depends on a distance to a desired anatomical structure, as well as a field of view captured by the image receivers 702.

Moreover, the angles (α) determine image convergence properties that generally translate into depth perception. At angles (α) that are greater than ten (10) degrees, the image convergence properties may cause the human eye not to be able to resolve a three-dimensional image. However, there may be situations with small-diameter cameras, cameras with specialty lenses, and display technology (e.g., software or hardware) that can enable depth perception at angles greater than 10 degrees, and possibly up to 80 degrees.

Figure 11:
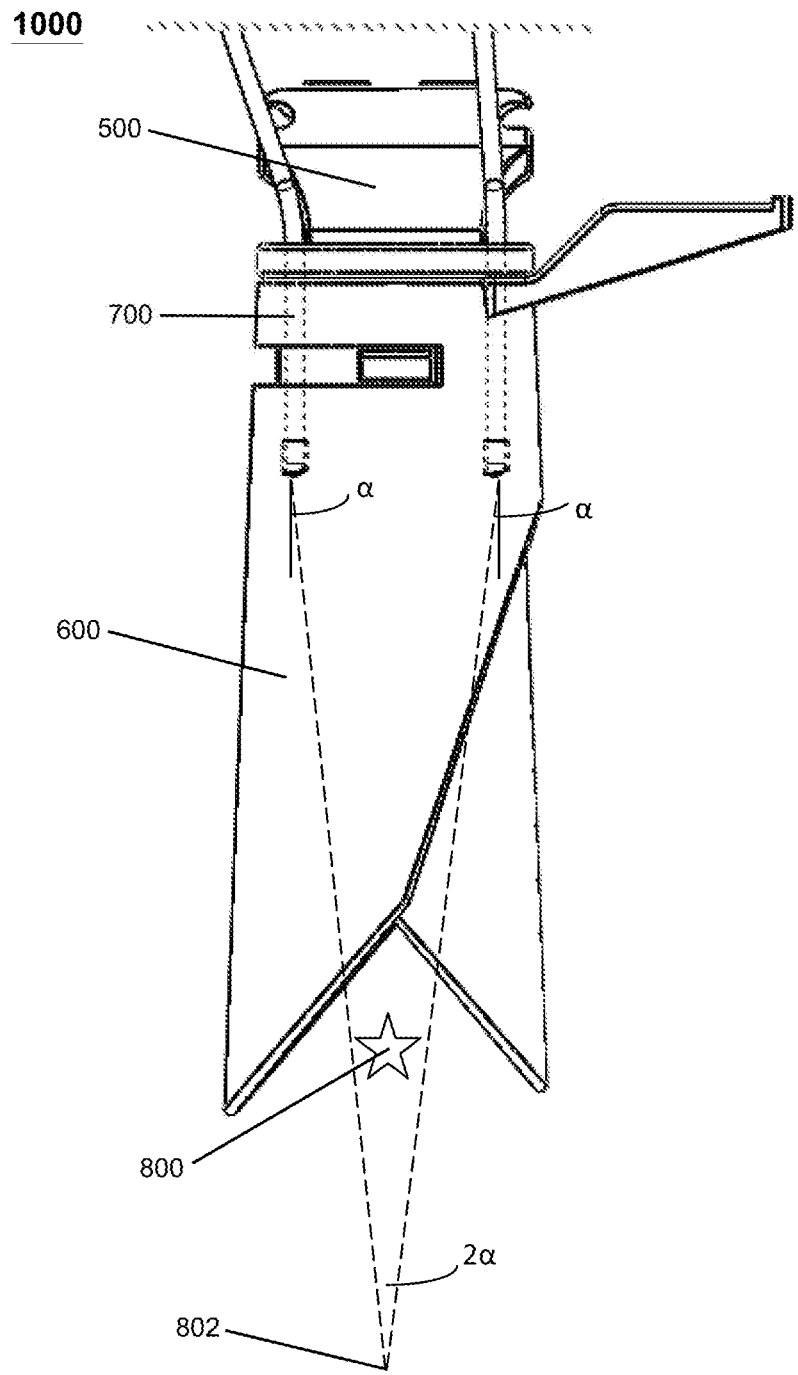
FIG. 11 illustrates a stereoscopic visualization portal system that includes the minimally invasive portal system of FIG. 8 with the portal component of FIG. 7 and the image sensors of FIGS. 9 and 10.

FIG. 11 illustrates a stereoscopic visualization portal system 1000. The stereoscopic visualization portal system 1000 includes the minimally invasive portal system 600 with the portal component 500, and the image sensors 700.

The image sensors 700 are rigidly secured in the channels 502 at angles α that eventually converge at point 802. In this regard, the angles α should be chosen so that the point 802 is at least a farthest accessible point in a particular surgical procedure. Consequently, image data of any anatomical structure or object 800 of interest to the surgeon can be within a depth perception range and can be captured at two distinct angles by the image sensors 700.

The image data of the respective image sensors 700 can then be transmitted to the corresponding eye of the surgeon as described herein. This enables the human brain of the surgeon to recreate a three dimensional image with depth perception that is similar to a normal biological function called stereopsis.

FIG. 12A illustrates the stereoscopic visualization portal system 1000 connected to an electronic processor (e.g., processing device) 900 and the example stereoscopic apparatus 100. Similarly, the electronic processor (e.g., processing device) 900 can connect the stereoscopic visualization portal system 1000 and the example stereoscopic apparatus 103.

As illustrated in FIG. 12A, the electronic processor (e.g., processing device) 900 is capable of receiving and transmitting the image data captured by the respective image sensors 700 to their corresponding electronic displays 200 of the stereoscopic apparatus 100 of FIG. 1A.

FIG. 12B illustrates the stereoscopic visualization portal system 1000 connected to an electronic processor (e.g., processing device) 900 and the example stereoscopic apparatus 101.

As illustrated in FIG. 12B, the electronic processor (e.g., processing device) 900 is capable of receiving and transmitting the image data captured by the respective image sensors 700 to their corresponding electronic displays 200 of stereoscopic apparatus 101 of FIG. 1B.

Figure 13:
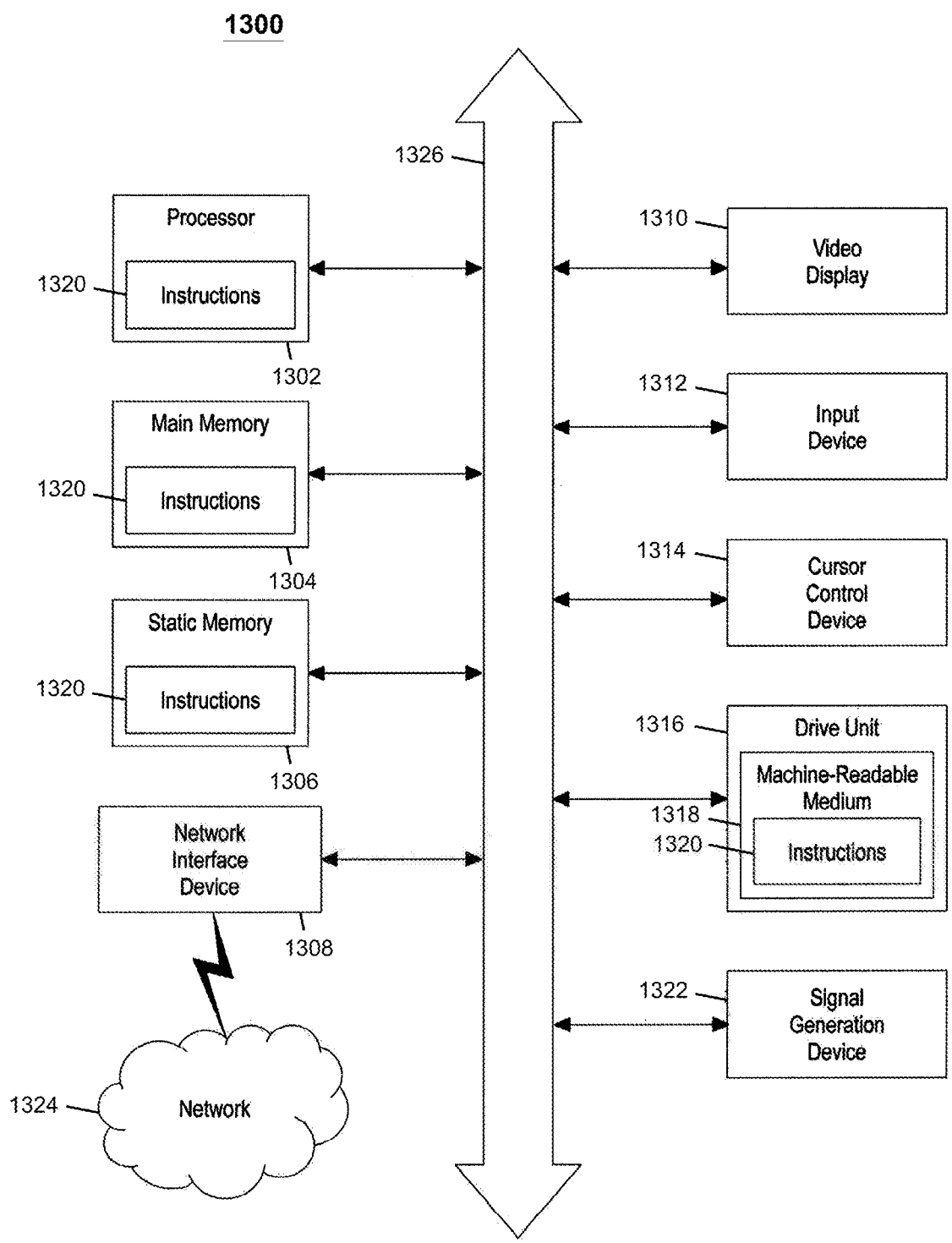
FIG. 13 illustrates a block diagram of an example general computer system.

FIG. 13 is a block diagram of an example general computer system 1300. The computer system 1300 can include a set of instructions that can be executed to cause the computer system 1300 to perform any one or more of the methods or computer based functions as disclosed herein in FIGS. 1A-12B. The computer system 1300, or any portion thereof, may operate as a standalone device or may be connected, e.g., using a network or other connection, to other computer systems or peripheral devices. For example, the computer system 1300 may be the processor 900, and may further be connected to other systems and devices, such as other computing system(s) via a network.

The computer system 1300 may also be implemented as or incorporated into various devices, such as a personal computer (PC), a tablet PC, a personal digital assistant (PDA), a mobile device (e.g., smartphone), a palmtop computer, a laptop computer, a desktop computer, a communications device, a control system, a web appliance, or any other machine capable of executing a set of instructions (sequentially or otherwise) that specify actions to be taken by that machine. Further, while a single computer system 1300 is illustrated, the term "system" shall also be taken to include any collection of systems or sub-systems that individually or jointly execute a set, or multiple sets, of instructions to perform one or more computer functions.

As illustrated in FIG. 13, the computer system 1300 may include a processor 1302, e.g., a central processing unit (CPU), a graphics-processing unit (GPU), or both. Moreover, the computer system 1300 may include a main memory 1304 and a static memory 1306 that can communicate with each other via a bus 1326. As shown, the computer system 1300 may further include a video display unit 1310, such as a liquid crystal display (LCD), an organic light emitting diode (OLED), a flat panel display, a solid state display, or a cathode ray tube (CRT). Additionally, the computer system 1300 may include an input device 1312, such as a keyboard, and a cursor control device 1314, such as a mouse. The computer system 1300 can also include a disk drive (or solid state) unit 1316, a signal generation device 1322, such as a speaker or remote control, and a network interface device 1308.

In a particular embodiment or aspect, as depicted in FIG. 13, the disk drive (or solid state) unit 1316 may include a computer-readable medium 1318 in which one or more sets of instructions 1320, e.g., software, can be embedded. Further, the instructions 1320 may embody one or more of the methods or logic as described herein. In a particular embodiment or aspect, the instructions 1320 may reside completely, or at least partially, within the main memory 1304, the static memory 1306, and/or within the processor 1302 during execution by the computer system 1300. The main memory 1304 and the processor 1302 also may include computer-readable media.

In an alternative embodiment or aspect, dedicated hardware implementations, such as application specific integrated circuits, programmable logic arrays and other hardware devices, can be constructed to implement one or more of the methods described herein. Applications that may include the apparatus and systems of various embodiments or aspects can broadly include a variety of electronic and computer systems. One or more embodiments or aspects described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments or aspects, the methods described herein may be implemented by software programs tangibly embodied in a processor-readable medium and may be executed by a processor. Further, in an exemplary, non-limited embodiment or aspect, implementations can include distributed processing, component/object distributed processing, and parallel processing. Alternatively, virtual computer system processing can be constructed to implement one or more of the methods or functionality as described herein.

It is also contemplated that a computer-readable medium includes instructions 1320 or receives and executes instructions 1320 responsive to a propagated signal, so that a device connected to a network 1324 can communicate voice, video or data over the network 1324. Further, the instructions 1320 may be transmitted or received over the network 1324 via the network interface device 1308.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment or aspect, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments or aspects, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Although specific example embodiments or aspects have been described, it will be evident that various modifications and changes may be made to these embodiments or aspects without departing from the broader scope of the invention. Accordingly, the specification and drawings are to be regarded in an illustrative rather than a restrictive sense. The accompanying drawings that form a part hereof, show by way of illustration, and not of limitation, specific embodiments or aspects in which the subject matter may be practiced. The embodiments or aspects illustrated are described in sufficient detail to enable those skilled in the art to practice the teachings disclosed herein. Other embodiments or aspects may be utilized and derived therefrom, such that structural and logical substitutions and changes may be made without departing from the scope of this disclosure. This Detailed Description, therefore, is not to be taken in a limiting sense, and the scope of various embodiments or aspects is defined only by the appended claims, along with the full range of equivalents to which such claims are entitled.

Such embodiments or aspects of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or aspects have been illustrated and described herein, it should be appreciated that any arrangement calculated to achieve the same purpose may be substituted for the specific embodiments or aspects shown. This disclosure is intended to cover any and all adaptations or variations of various embodiments or aspects. Combinations of the above embodiments or aspects, and other embodiments or aspects not specifically described herein, will be apparent to those of skill in the art upon reviewing the above description.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments or aspects, various features are grouped together in a single embodiment for the purpose of streamlining the disclosure. This method of disclosure is not to be interpreted as reflecting that the claimed embodiments or aspects have more features than are expressly recited in each claim. Rather, as the following claims reflect, inventive subject matter lies in less than all features of a single disclosed embodiment or aspect. Thus the following claims are hereby incorporated into the Detailed Description, with each claim standing on its own as a separate example embodiment or aspect. It is contemplated that various embodiments or aspects described herein can be combined or grouped in different combinations that are not expressly noted in the Detailed Description. Moreover, it is further contemplated that claims covering such different combinations can similarly stand on their own as separate example embodiments or aspects, which can be incorporated into the Detailed Description.

The invention claimed is:

1. A stereoscopic visualization portal system comprising:
a portal including a first aperture, the portal configured to create a surgical channel extending from the first aperture into a patient through which instrumentation is insertable to perform a surgical procedure;
a portal component including a second aperture and a plurality of channels, the second aperture defined about an axis and the plurality of channels disposed about the second aperture, the channels including a first channel and a second channel extending along the axis below the second aperture, the portal component connectable to the portal such that the second aperture communicates with the first aperture and the channels extend through the first aperture into the surgical channel of the portal;
a first image sensor secured within the first channel in the surgical channel at a first angle with respect to the axis and directed inwardly toward a location below the portal;
a first cable extending from the first image sensor to transmit first image data obtained by the first image sensor;
a second image sensor secured within the second channel in the surgical channel at a second angle with respect to the axis and directed inwardly toward the location, the first angle and the second angle converging at the location and configured to define a depth of perception of the surgical procedure with respect to the surgical channel of the portal;
a second cable extending from the second image sensor to transmit second image data obtained by the second image sensor;
a first display structure disposed in proximity to a first eye aperture of an eyeframe to present the first image data through the first eye aperture; and
a second display structure disposed in proximity to a second eye aperture of the eyeframe to display the second image data through the second eye aperture, wherein a view that is external to the first display structure and the second display structure is visible through the first eye aperture and the second eye aperture, and wherein the first image data and the second image data are visible through the first eye aperture and the second eye aperture enabling formation of a stereoscopic view of an anatomical structure disposed within the depth of perception.

2. The stereoscopic visualization portal system of claim 1, wherein the first display structure and the second display structure are angulated with respect to the eyeframe.

3. The stereoscopic visualization portal system of claim 1, wherein the system further comprises a first display aperture proximate to the first eye aperture, and a second display aperture proximate to the second eye aperture.

4. The stereoscopic visualization portal system of claim 1, wherein
the first display structure includes a first magnifying apparatus and a first electronic display, the first magnifying apparatus disposed in relation to the first aperture at a first end of the first magnifying apparatus and proximately to the first electronic display at a second end of the first magnifying apparatus; and
the second display structure includes a second magnifying apparatus and a second electronic display, the second magnifying apparatus disposed in relation to the second aperture at a first end of the second magnifying apparatus and proximately to the second electronic display at a second end of the second magnifying apparatus.

5. The stereoscopic visualization portal system of claim 1, wherein the system further comprises:
a processing device including a first incoming data port configured to receive the first image data and a second incoming data port configured to receive the second image data, the first incoming data port connected to the first cable and the second incoming data port connected to the second cable, the processing device further including a first outgoing data port configured to transmit the first image data to a first electronic display and a second outgoing data port configured to transmit the second image data to a second electronic display.

6. The stereoscopic visualization portal system of claim 1, wherein the first display structure and the second display structure are angulated with respect to each other.

7. The stereoscopic visualization portal of claim 1, wherein when the portal is disposed over the anatomical structure, the location at which the first image sensor and the second image sensor converge is a point in relationship to the anatomical structure such that the stereoscopic view of the anatomical structure is capable of being formed within the depth of perception.

8. The stereoscopic visualization portal system of claim 7, wherein the first angle and the second angle are based on a distance to the point and a distance between the first image sensor and the second image sensor.

9. The stereoscopic visualization portal system of claim 1, wherein the system further comprises:
a first magnifying apparatus and a first electronic display, the first magnifying apparatus disposed in relation to the first display aperture and connected to the first electronic display at a first end of the first magnifying apparatus; and
a second magnifying apparatus and a second electronic display, the second magnifying apparatus disposed in relation to the second display aperture and connected to the second electronic display at a first end of the second magnifying apparatus.

10. The stereoscopic visualization portal system of claim 9, wherein:
the first display structure includes a first mirror structure disposed proximately to a second end of the first magnifying apparatus, and
the second display structure includes a second mirror structure disposed proximately to a second end of the second magnifying apparatus.

11. The stereoscopic visualization portal system of claim 10, wherein the first mirror structure comprises:
a first mirror and a second mirror, the first mirror and the second mirror each angled at forty five degrees with respect to a vertical plane separating the first mirror from the second mirror, the second mirror being disposed proximately to the first eye aperture.

12. The stereoscopic visualization portal system of claim 10, wherein the second mirror structure comprises:
a first mirror and a second mirror, the first mirror and the second mirror each angled at forty five degrees with respect to a vertical plane separating the first mirror from the second mirror, the second mirror being disposed proximately to the second eye aperture.

\* \* \* \* \*